US008402965B1

(12) United States Patent
Scharfenberg et al.

(10) Patent No.: US 8,402,965 B1
(45) Date of Patent: Mar. 26, 2013

(54) MASS OXYGEN DISTRIBUTION SYSTEM

(75) Inventors: Randolph E. Scharfenberg, Chesterfield, MO (US); Anthony Francis Giordano, St. Louis, MO (US)

(73) Assignee: Essex Cryogenics of Missouri, Inc., St. Louis, MI (US)

( * ) Notice: Subject to any disclaimer, the term of this patent is extended or adjusted under 35 U.S.C. 154(b) by 488 days.

(21) Appl. No.: 12/657,682

(22) Filed: Jan. 26, 2010

Related U.S. Application Data

(60) Provisional application No. 61/206,376, filed on Jan. 30, 2009.

(51) Int. Cl.
*A62B 7/06* (2006.01)
*A62B 7/00* (2006.01)
*A61M 16/00* (2006.01)

(52) U.S. Cl. .......... 128/201.21; 128/204.17; 128/204.18

(58) Field of Classification Search ............. 128/201.21, 128/204.17, 204.18, 204.21
See application file for complete search history.

(56) References Cited

U.S. PATENT DOCUMENTS

| 2,039,901 A | 5/1936 | Hawley |
| 2,500,249 A | 3/1950 | Hansen |
| 2,702,546 A | 2/1955 | Gilroy et al. |
| 3,791,403 A | 2/1974 | Folkerth |
| 3,976,227 A | 8/1976 | Ray |
| 4,165,738 A | 8/1979 | Graves et al. |
| 4,211,086 A | 7/1980 | Leonard et al. |
| 4,510,930 A | 4/1985 | Garcia |
| 4,899,546 A * | 2/1990 | Eigenbrod ...................... 62/50.2 |
| 4,944,292 A | 7/1990 | Gaeke et al. |
| 5,057,822 A | 10/1991 | Hoffman |
| 5,101,820 A | 4/1992 | Christopher |
| 5,293,896 A | 3/1994 | Gliechmann et al. |
| 5,396,885 A | 3/1995 | Nelson |
| 5,511,542 A * | 4/1996 | Hall ......................... 128/201.21 |
| 5,979,440 A | 11/1999 | Honkonen et al. |
| 6,220,244 B1 | 4/2001 | McLaughlin |
| 6,354,294 B1 | 3/2002 | Villareal, Jr. |
| 6,681,764 B1 * | 1/2004 | Honkonen et al. ........ 128/201.21 |
| 6,742,517 B1 * | 6/2004 | Frye et al. ................ 128/201.21 |

* cited by examiner

*Primary Examiner* — Nicholas Lucchesi
*Assistant Examiner* — Leah Stohr
(74) *Attorney, Agent, or Firm* — Peter S. Gilster; Greensfelder, Hemker & Gale, P.C.

(57) ABSTRACT

A mass oxygen distribution system ("MODS") for mass delivery and distribution for of breathing oxygen has a mobile unit that stores a large amount of on board LOX and controls distribution of oxygen from the enclosure at safe pressure to one or more patient end users. An on board oxygen converter source within the enclosure stores preferably up to 75-liters of LOX, ready to be volatilized to provide gaseous oxygen for many hours. The enclosure being supported by wheeled support members, allowing the enclosure to be moved to and through premises where mass distribution to said one or more end users is required and quickly put into use. LOX in the pressurized vessel is provided to one of a dual set of vaporizers converts the liquid oxygen to cold gaseous breathing oxygen. A dual coil heat exchanger warms the cold breathing oxygen to safe breathing temperature. A warning system monitors temperature and pressure of the breathing oxygen. Dual auxiliary oxygen sources can be connected to the mobile unit and continuous oxygen supply can be maintained for hours or days by switching between the auxiliary sources such as of the VGL type. The dual vaporizer sets allow continuous vaporizing. The oxygen is distributed by specialized hose assembly to multiple patient distribution kits even if patients are scattered in various locations.

8 Claims, 11 Drawing Sheets

MASS OXYGEN DISTRIBUTION SYSTEM

CROSS-REFERENCE TO RELATED APPLICATION

This application is based upon and claims the priority of U.S. provisional patent application Ser. No. 61/206,376, entitled MASS OXYGEN DISTRIBUTION SYSTEM, filed Jan. 30, 2009, and incorporated by reference herein.

TECHNICAL FIELD

The invention is in the field of breathing oxygen distribution systems and more particular relates to a liquid oxygen storage and delivery system for mass distribution of breathing oxygen for medical purposes.

That field is different from the field of supplying oxygen from small portable bottles intended for a single patient as in ambulance-type or "medevac" purposes such as in evacuation aircraft (e.g., air ambulance). The invention does not relate to home oxygen generator equipment. So also, it does not relate to resuscitator systems as in fire and rescue which supply breathing air but are not useful for supplying pure breathing oxygen to patients for medical use.

The invention differs also from typical installed hospital or clinical systems having permanent breathing oxygen distribution conduits, but the inventive system might be used to replace or supplement such installed medical systems in the event of an emergency or major system failure of an installed hospital or clinical system.

BACKGROUND

Mass patient situations in which breathing oxygen should be made available to multiple patients are possible and for which there should be planning including provision for supplying breathing oxygen. Such a situation might be a mass casualty incident where many patients need emergency treatment, that is, where there is a mass patient need. A temporary facility such as a field hospital might be set up for a mass casualty or location where, for example, patients will be given medical attention for an indefinite period whether of a few hours or many hours. Or there could be situations in any building or premises in which a medically emergent situation might occur, such as (for just one of many possible examples) a temporary triage medical location or emergency premises where multiple patients are to be supplied with breathing oxygen. Without intent to limit the possible premises in which there could be an emergent situation where patients might need to be administered breathing situation, such premises could, for example, be a hospital, temporary hospital, field hospital, factory building, office building, hotel or other multiple story residence, such as of the type in which condominiums and apartments might be present. In such examples, the logistics of bringing in oxygen equipment can be a challenge. Premises can have passages, doors or other architecture that will challenge or make difficult movement or location/relocation of any oxygen equipment that could supply oxygen for many patients.

Another challenge for providing oxygen to patients in such settings is that personnel in charge of providing medical oxygen might not know in advance how many patients will need to be supplied, and where they might be located. Patients could be separated by walls, rooms or on different floors or in other locations where the need is present but where there could be a substantial distance between a patient and a sufficient source of oxygen.

In a similar sense, a challenge for providing oxygen to patients in such settings is that the time duration of need for oxygen might not be predictable. In the case of chemical spills or where damage has occurred that might take an indefinite time to remediate sufficiently to move patients to another location, oxygen might need to be supplied not only quickly but for an indefinite time without being uninterrupted. Problems can arise if oxygen must be supplied from large replenishment sources such as trucked-in large tanks, and then rerouted to mass oxygen system capable of handling gas cryogenic supplies.

In mass casualties or situations where there are an indefinite number of casualties, some of whom might be isolated from one another and yet must be supplied from oxygen in a reliable manner that does not require continuous individual monitoring, or where individual attention is not possible but must be centrally monitored by minimum number of attendants or medical personnel, the use of known types of individual patient oxygen cylinders can be completely unacceptable or impossible. Instead, mass oxygen distribution is preferable, and a quickly deployable system for reliably assured and precisely controlled mass oxygen distribution for an indefinite time is desirable.

SUMMARY

Among the advantages, benefits, features, goals and objectives relative to the present invention are:

the provision of a complete liquid oxygen storage and delivery system for mass distribution of breathing oxygen system for mass oxygen distribution;

the provision of such a rapidly deployable system capable of quickly providing a long term patient mass oxygen supply in a wide variety of exigent situations as hereinabove mentioned;

the provision of such a mass oxygen distribution system that can seamlessly, that is, without interruption, deliver such breathing oxygen to large numbers of patients (mass long term distribution) from on board LOX supply, while also permitting connection of multiple independent variable gas/liquid (VGL) sources for filling or refilling the on board LOX supply; and for distributing breathing oxygen from LOX provided by said VGL sources;

the provision of such a mass oxygen distribution system having a mobile unit containing on board a large amount of liquid breathing oxygen, i.e., as herein described, about at least 75 L of LOX;

the provision of a mass oxygen distribution system a mobile unit having on board storage of a large amount of liquid breathing oxygen while providing both portability and mobility combined with continuous oxygen flow comparable to a hospital-scale emergency oxygen system;

the provision of such a mass oxygen distribution system that can be so supplied by such VGL auxiliary sources while delivering oxygen simultaneously to multiple patients;

the provision of such an oxygen distribution system that supplies oxygen from either an on board or one or more auxiliary LOX sources to patients at both safely controlled temperature and safely controlled pressure;

the provision of such a mass oxygen distribution system that includes a mobile MODS apparatus having a large on board amount of liquid breathing oxygen that is easily mobile, simple to move around, and precisely dimensioned to fit easily through premises and through most doorways, and so can rapidly be brought into action;

the provision of such a mass oxygen distribution system that includes a MODS mobile unit, containing a large on board amount of liquid breathing oxygen, that is constructed of rugged materials including aluminum;

the provision of such a mass oxygen distribution system that includes a mobile MODS apparatus that will withstand extreme emergency situations and environments;

the provision of such a mass oxygen distribution system that meets government standards and requirements for safe transport;

the provision of such a mass oxygen distribution system that includes a mobile unit that is tire-supported by casters having tires with "run flat" capability for resistance to tire punctures, and employs such tires that can be pushed easily over uneven surfaces, and the tires being on wheels with built-in locks for stability;

the provision of such a mass oxygen distribution system that includes a mobile MODS alarm system that does not require outside electrical power (such as AC power) but instead runs on internal batteries;

the provision of a mass oxygen distribution system that includes a mobile MODS mobile unit that can be carried by trailer for safe and rapid transport, including transport to remote locations;

the provision of such a mass oxygen distribution system that includes a mobile unit providing oxygen flow adjustability over a range suitable to the needs of medically challenging patient, and where such flow can be adjusted preferably in the range of 0-15 LPM;

the provision of such a mass oxygen distribution system that includes a mobile unit capable of powering pneumatic ventilators and other medical apparatus;

the provision of such a mass oxygen distribution system that includes a mobile unit that easily interfaces with oxygen supply masks, cannulas, simulators, pneumatic and electronic ventilators and various other life support products;

the provision of a mass oxygen distribution system that includes a mobile MODS apparatus having hoses for connection to remote patients and equipment;

Briefly, the present invention provides a mass breathing oxygen distribution system, and is herein termed "mass oxygen distribution system" ("MODS") and provides a key mobile oxygen system central control and supply component for supplying, controlling and enabling mass breathing oxygen distribution to multiple patients. The mobile, wheel-supported main MODS component (referred herein as the "MODS mobile unit" or "mobile apparatus") contains a large on board amount (such as at least about 75 L of LOX) and is capable of supplying breathing oxygen obtained from said on board storage, or alternatively from external auxiliary sources such as VGL (variable gas/liquid) storage, at controlled high flow rates and at controlled temperature and pressure for an extended period of time by use of either on board oxygen storage or external oxygen sources. When the MODS mobile is combined with certain accessories shown in the drawings there is then realized a complete MODS gaseous oxygen system (in this description termed "complete MODS system" or "the complete system") very quickly and conveniently capable of supplying and distributing breathing oxygen to multiple patients during a mass casualty incident or in a field hospital that might be set up in a mass casualty or location where, for example, patients will be given medical attention for an indefinite period whether of a few hours or many hours. The MODS system and apparatus is intended to have capability of being rapidly deployable and easily and quickly capable use in any a wide variety of buildings or different types of premises where an emergent situation might be present, such as for one of many possible examples a temporary or triage medical facility or emergency premises where multiple patients are to be supplied with breathing oxygen.

Other features will be in part apparent and in part pointed out below and will be found illustrated in the drawings of this disclosure which are briefly described below.

Elements identified are:
- 11 (Burst Disc)
- 12 (Liquid Oxygen Converter)
- 32 (Filler Valve)
- 34 (Outlet Pressure Gauge)
- 35 (Outlet Shut off & Vent Valve)
- 38 (Outlet Quick Disconnect Valve)
- 39 (Pressure Gauge Relief Valve)
- 42 (Vaporizer Bank 1)
- 43 (Vaporizer Bank 2)
- 44 (Dual Coil Heat Exchanger)
- 47 (Temperature Transducer)
- 48 (Pressure Transducer)

Figure 1:
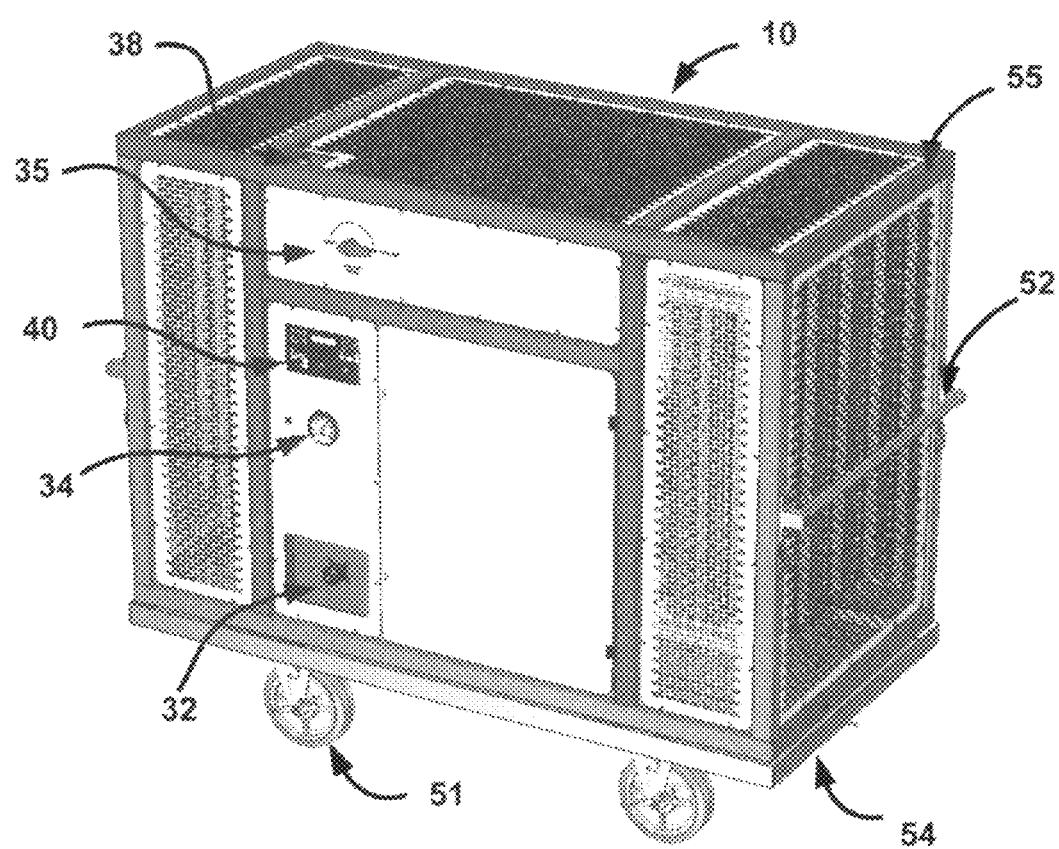
FIG. 1 is a perspective view of the new MODS liquid oxygen storage and delivery system mobile unit constructed in accordance with and embodying the present invention.
Elements identified are:
10 (MODS 75 System Mobile Unit)
32 (Filler Valve)
34 (Outlet Pressure Gauge)
35 (Outlet Shut off & Vent Valve)
38 (Outlet Quick Disconnect Valve)
40 (LOX Quantity Indicator and Alarm System)
41 (AC Adapter Port)
51 (Casters)
52 (Handle)
54 (Water Catch Pan)
Figure 5:
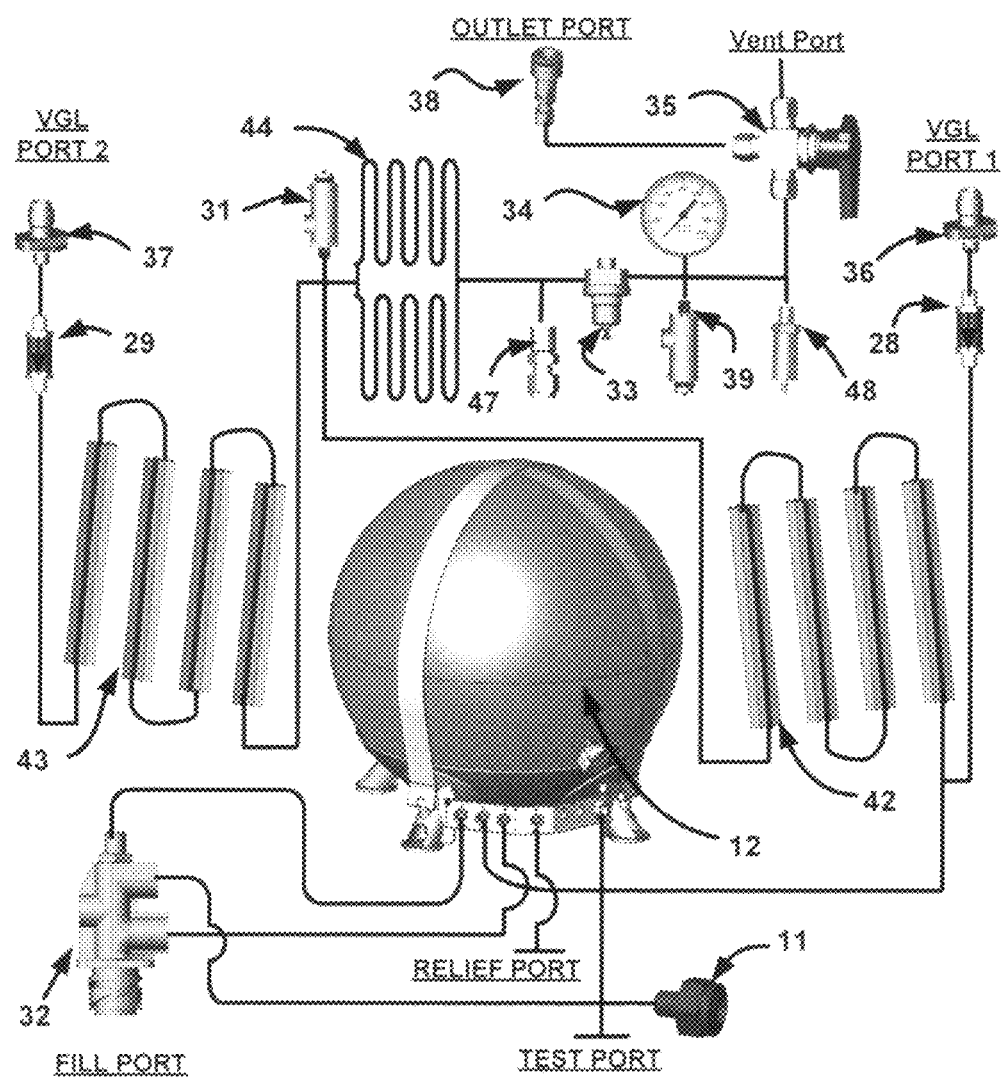
FIG. 5 is a schematic diagram of components of the system of FIG. 1 with the various elements thereof shown and labeled.
Figure 5A:
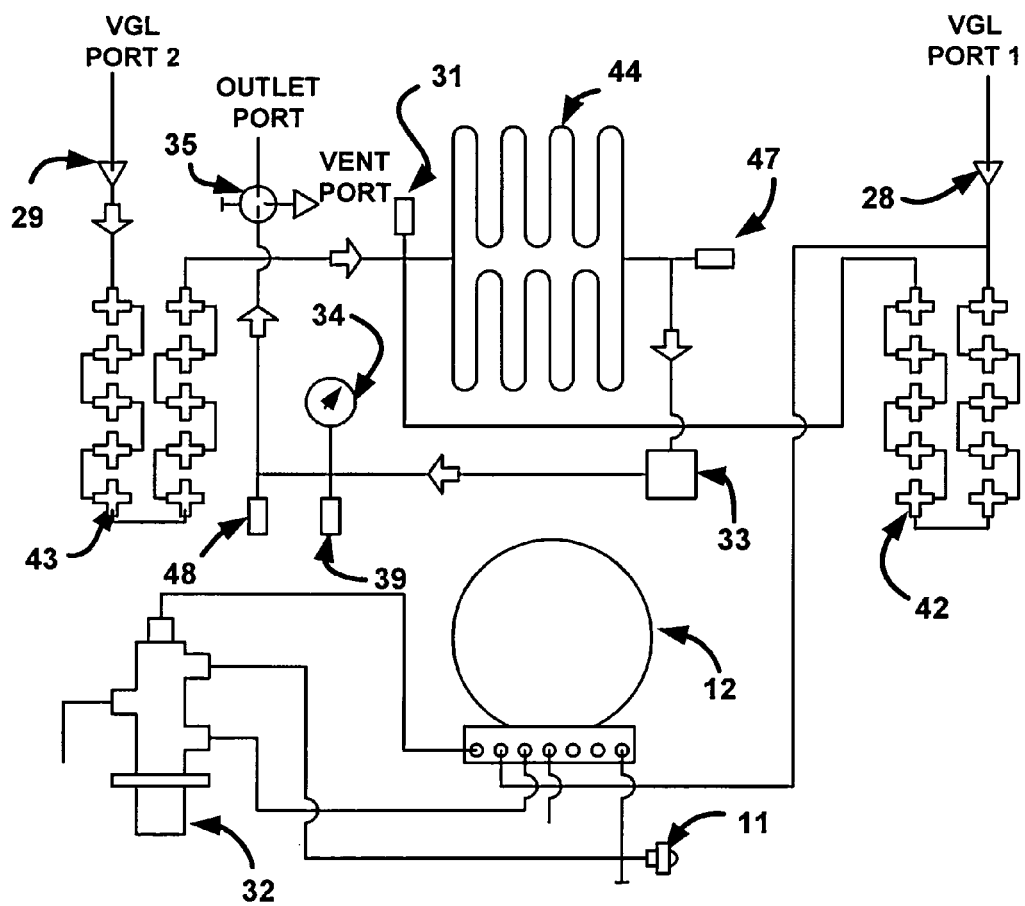

FIG. 5A is an alternate schematic diagram of the liquid oxygen system of FIG. 1 with the various elements of FIG. 5 shown in relative functional physical relationship.

Figure 6:
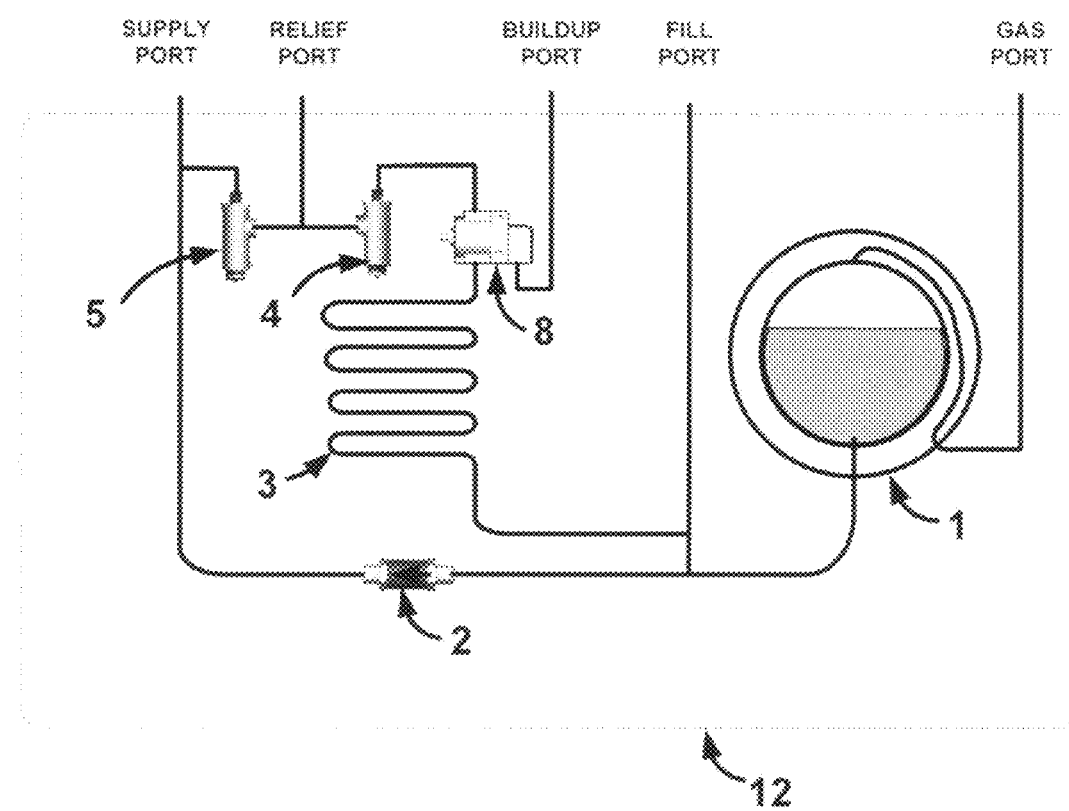

FIG. 6 is a schematic diagram of the liquid oxygen converter 12 with the various elements thereof shown and labeled.
- 1 (Liquid oxygen Container)
- 2 (Supply Line Check Valve)
- 3 (Pressure Buildup Coil)
- 4 (Primary Relief Valve)
- 5 (Secondary Relief Valve)
- 8 (Pressure Closing Valve)
- 12 (Liquid Oxygen Converter)

Figure 7:
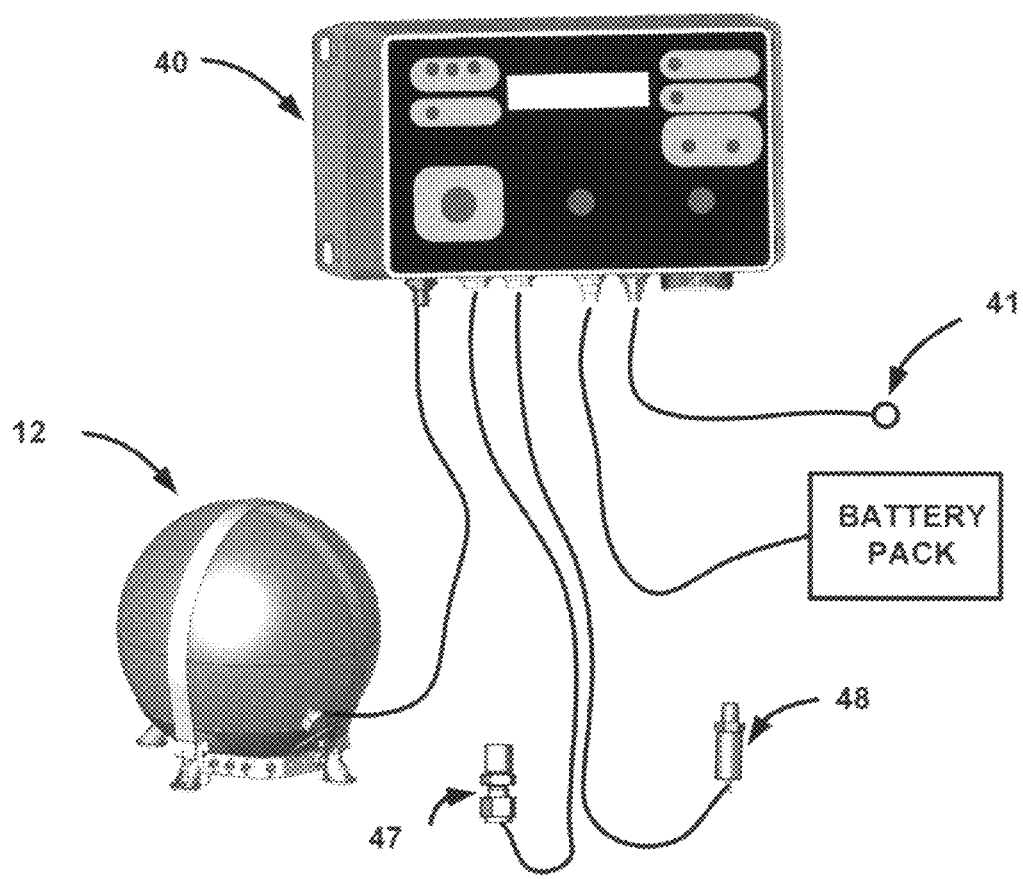

FIG. 7 is a schematic diagram of the liquid oxygen (LOX) quantity indicator and alarm system 40 with various elements thereof shown and labeled.

Elements identified are:
- 12 (Liquid Oxygen Converter)
- 40 (LOX Quantity Indicator and Alarm System)
- 41 (AC Adapter Port)
- 47 (Temperature Transducer)
- 48 (Pressure Transducer)

Figure 8:
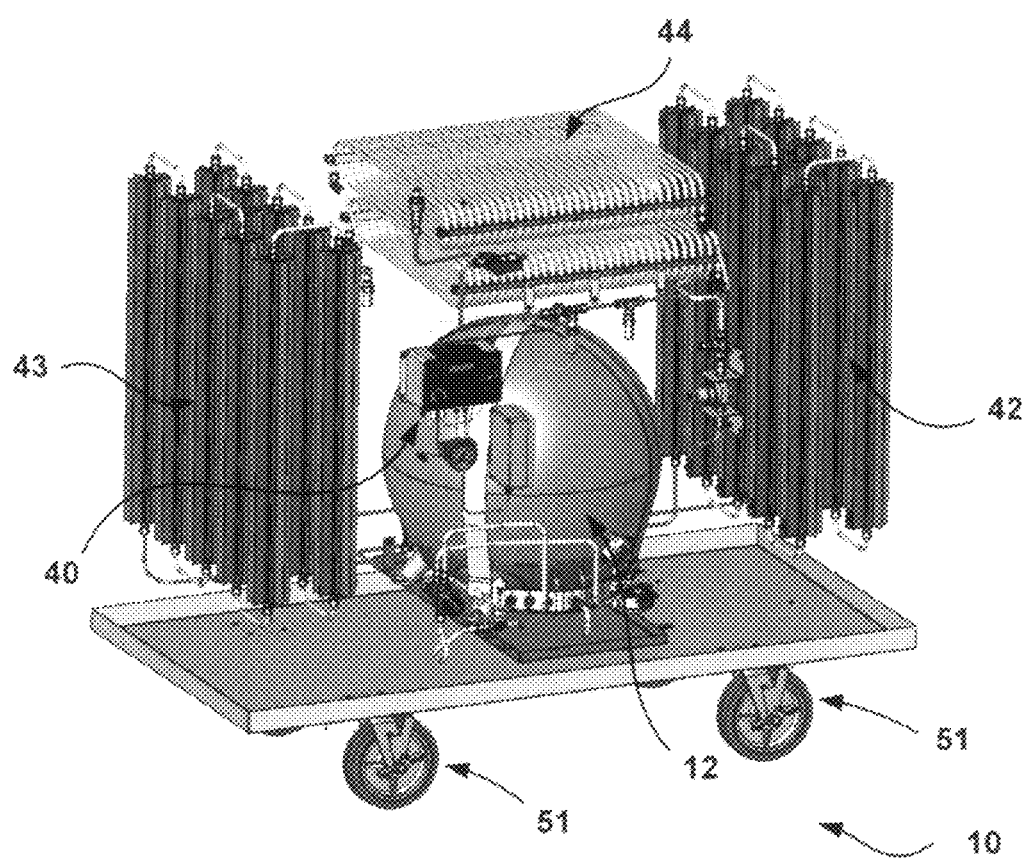

FIG. 8 is a perspective of internal components of the MODS liquid oxygen storage and delivery system mobile unit, but with its external housing and various control and alarm components not shown to permit viewing of other components.

Figure 9:
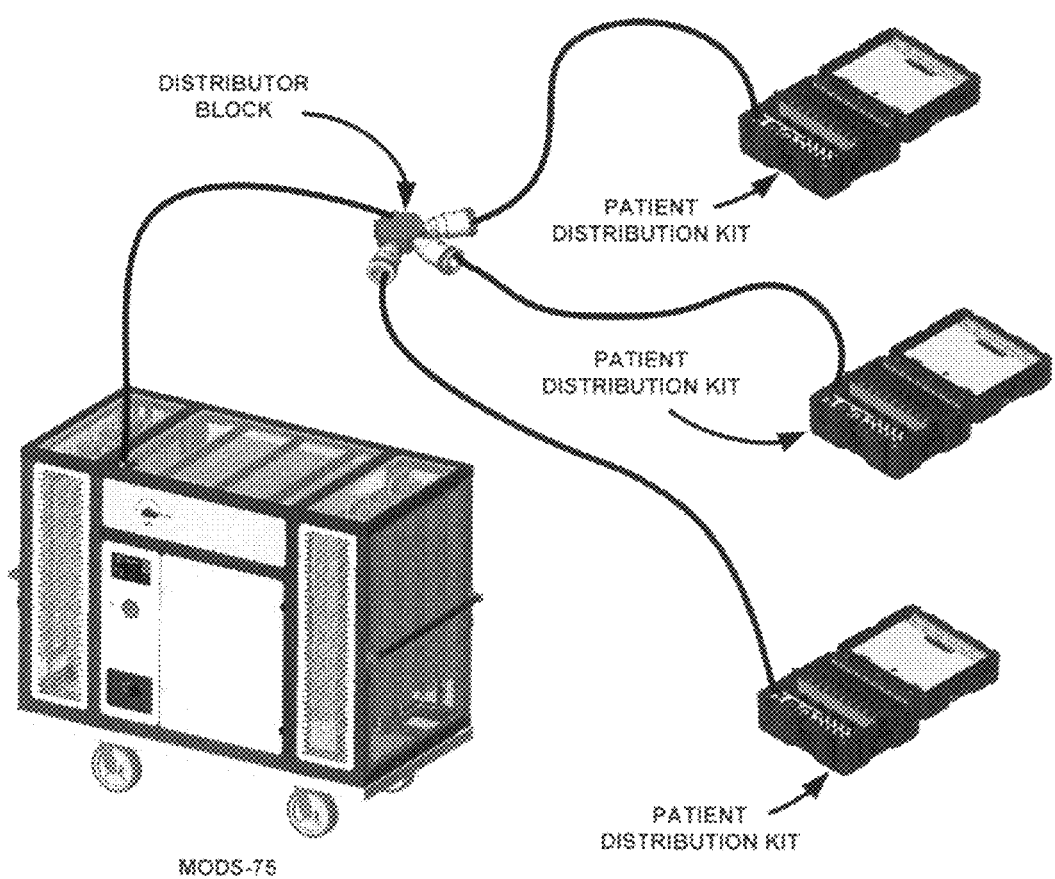

FIG. 9 is a system block diagram showing various interconnected components of the MODS liquid oxygen storage and delivery system including the mobile unit, with the various components connected for mass distribution of patient breathing oxygen.

Figure 10:
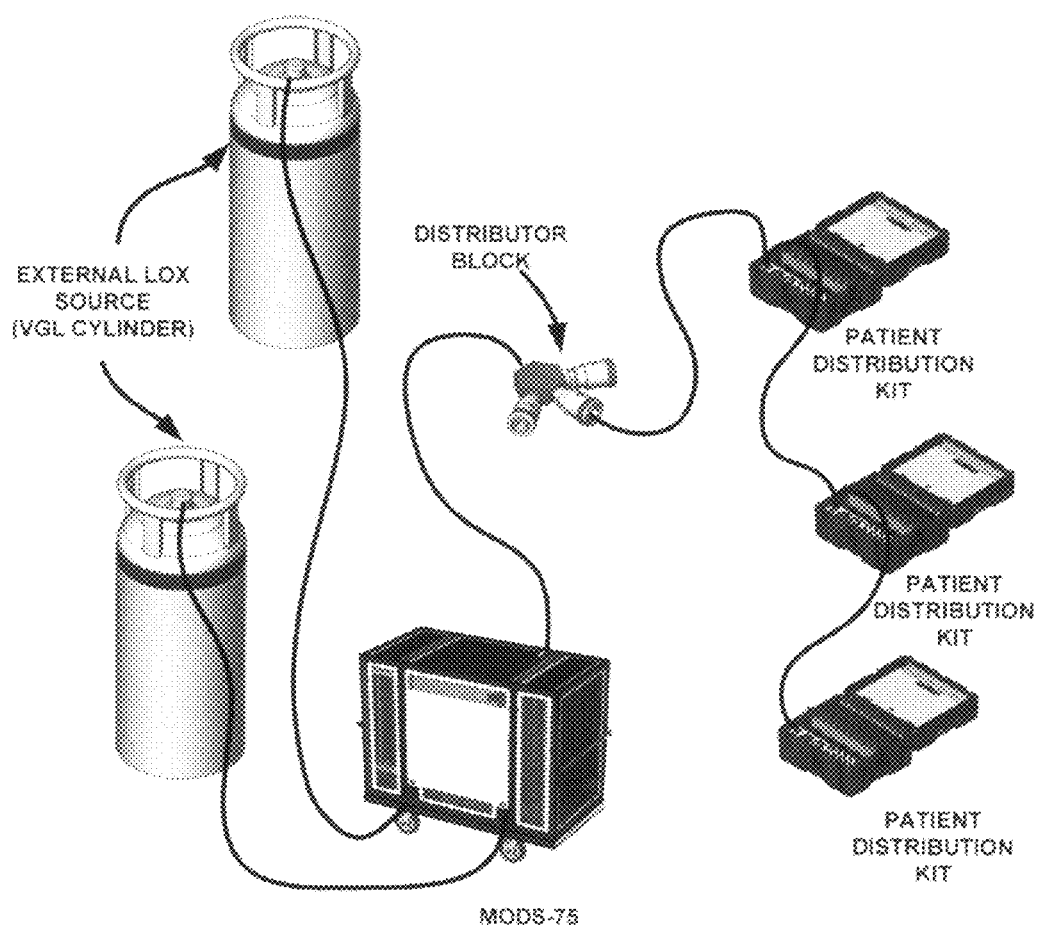

FIG. 10 is a system block diagram showing such interconnected components of the MODS liquid oxygen storage and delivery system including the mobile unit, and where the mobile unit is shown being supplied with either of VGL oxygen sources.

Corresponding reference characters indicate corresponding parts in multiple figures of the drawings.

DESCRIPTION OF PRACTICAL EMBODIMENTS

The present mass breathing oxygen distribution system is herein termed "mass oxygen distribution system" ("MODS") and provides a key mobile oxygen system central control and supply component referred to herein as the "MODS mobile unit" or "mobile apparatus" for supplying, controlling and enabling mass breathing oxygen distribution to multiple patients. The MODS mobile unit 10 is capable of supplying breathing oxygen at high flow rates for an extended period of time by use of either stored on board oxygen or external oxygen sources which feed or supplement the mobile unit. In any event, the user-operator is provided with oxygen flow suitable to the needs of medically challenging patient or patients.

When the MODS mobile unit is combined with certain accessories shown in the drawings it forms a complete MODS gaseous oxygen system (in this description termed "complete MODS system" or "the complete system") as shown in the system block diagram, FIG. 9, it is capable of supplying and distributing breathing oxygen to multiple patients during a mass casualty incident or in a temporary or so-called field hospital that might be set up in a mass casualty or location where, for example, patients will be given medical attention for an indefinite period whether of a few hours or many hours.

The MODS system and mobile unit is intended to have capability of use in any a wide variety of buildings or different types of premises where an emergent situation might be present, such as for one of many possible examples a temporary or triage medical facility or emergency premises where multiple patients are to be supplied with breathing oxygen.

Thus, referring to the drawings, the MODS system, in its entirety, is comprised of major components; that are the MODS mobile unit 10 itself as combined with components termed "multiple patient distribution kits" ("PDK") illustrated in the drawings and an optional hose assembly (termed "HA"). These components and their functions are described in further detail in a system outline section of this disclosure. If the MODS must be located relatively far away from patients, then a further component of the complete system is the hose assembly (termed "HA") providing according to a preferred design a 100-foot hose extension. The HA can take the form of a hose reel assembly ("HRA") that can be used to extend oxygen distribution from the MODS mobile unit up to a distance, for example, of 100 feet of selective extension. The HRA or HA can also be used between multiple PDK's. If not required, the HRA or HA need not be used as part of the MODS system.

FIGS. 1-4 well illustrate that the MODS mobile unit is easily and quickly movable. It is provided, as shown, with four caster wheels 31 at the four corners. It is designed specifically so that it has a 30-inch width (narrowest dimension), despite its other substantial size required to hold a large amount of LOX. This allows the MODS mobile unit to fit easily though most doorways. The tire-supported unit has casters having tires with "run flat" capability for resistance to tire punctures. The tires that can be pushed easily over uneven surfaces, and are on wheels with built-in locks for stability.

The MODS system and mobile unit mass oxygen distribution system have been designed to meet government standards and requirements for safe transport so as to be quickly brought to a location of use and rapidly put into operation.

Because MODS mobile unit has on board capacity to store a large amount of liquid oxygen ("LOX") such as most preferably 75 liters of LOX maintained in a spherical pressurized vessel converter system designated at 12, there is sufficient oxygen for hours of operation. LOX is retained under pressure at very cold temperatures maintaining the liquid state. The LOX is controllably released in a gaseous oxygen state for being distributed to patients by PDK use no matter whether patients are scattered in various locations, making use of the HRA and/or HA components. The PDKs provide oxygen flow adjustment for patients.

With reference to the drawings, FIGS. 1-4 illustrates system 10 in an assembled or at least partially assembled condition. FIG. 5 schematically represents the arrangement of most elements of system 10, while FIG. 6 schematically represents the elements of the oxygen container subsystem 12. FIG. 7 schematically represents the arrangement of most elements of the LOX quantity indicator and microprocessor-controlled alarm electrical system 40, which operates on batteries (shown in FIG. 7) within the unit. For clarity and simplicity of the figures, not all the elements are shown and/or labeled in every figure.

Figure 2:
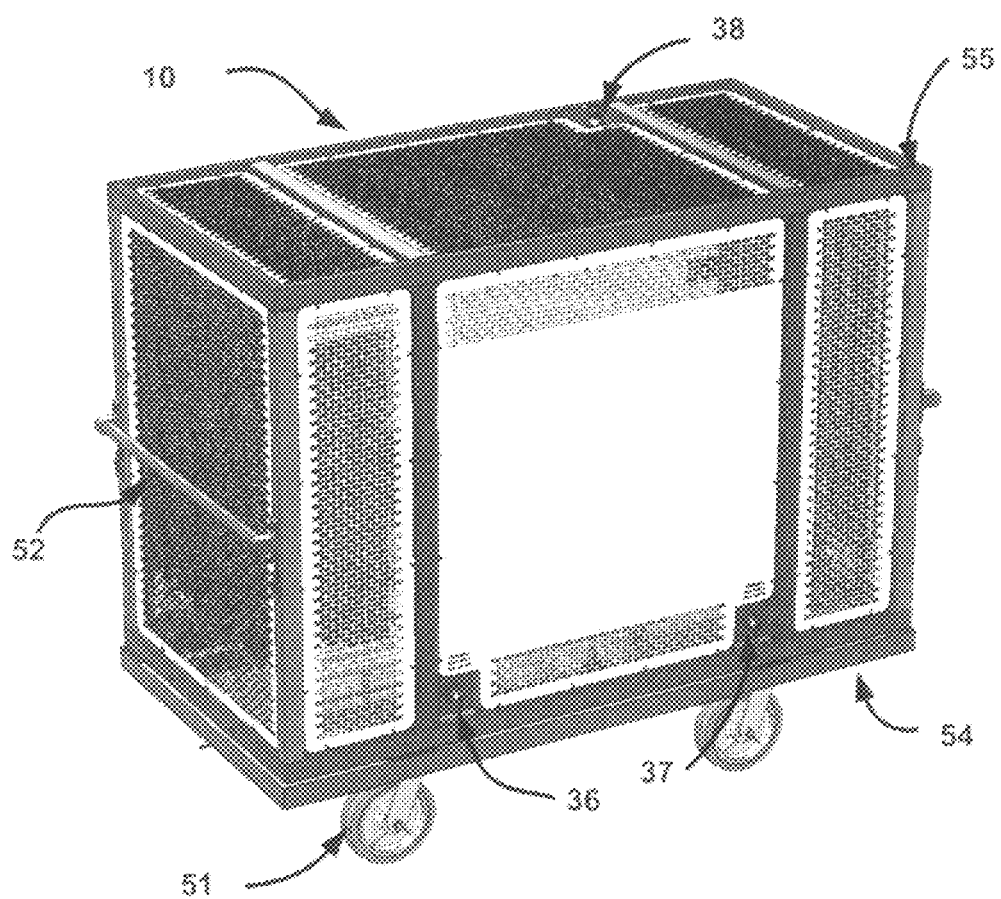
FIG. 2 is a rear perspective view, of the new liquid oxygen storage and delivery system mobile unit constructed in accordance with and embodying the present invention.
Elements identified are:
10 (MODS 75 System Mobile Unit)
36 (External VGL port 1)
37 (External VGL port 2)
38 (Outlet Quick Disconnect Valve)
51 (Casters)
52 (Handle)
54 (Water Catch Pan)
55 (Frame Housing)

The frame housing 55, as shown in FIGS. 1-2, is preferably welded of aluminum extrusion in a preferred generally rectangular shape. The frame housing 55 is the structural support for all the elements of system 10. The water catch pan 54, casters 51, and handle 52 attach directly to the frame housing 55. These built-in accessories contribute to portability/mobility of the LOX system 10.

Figure 3:
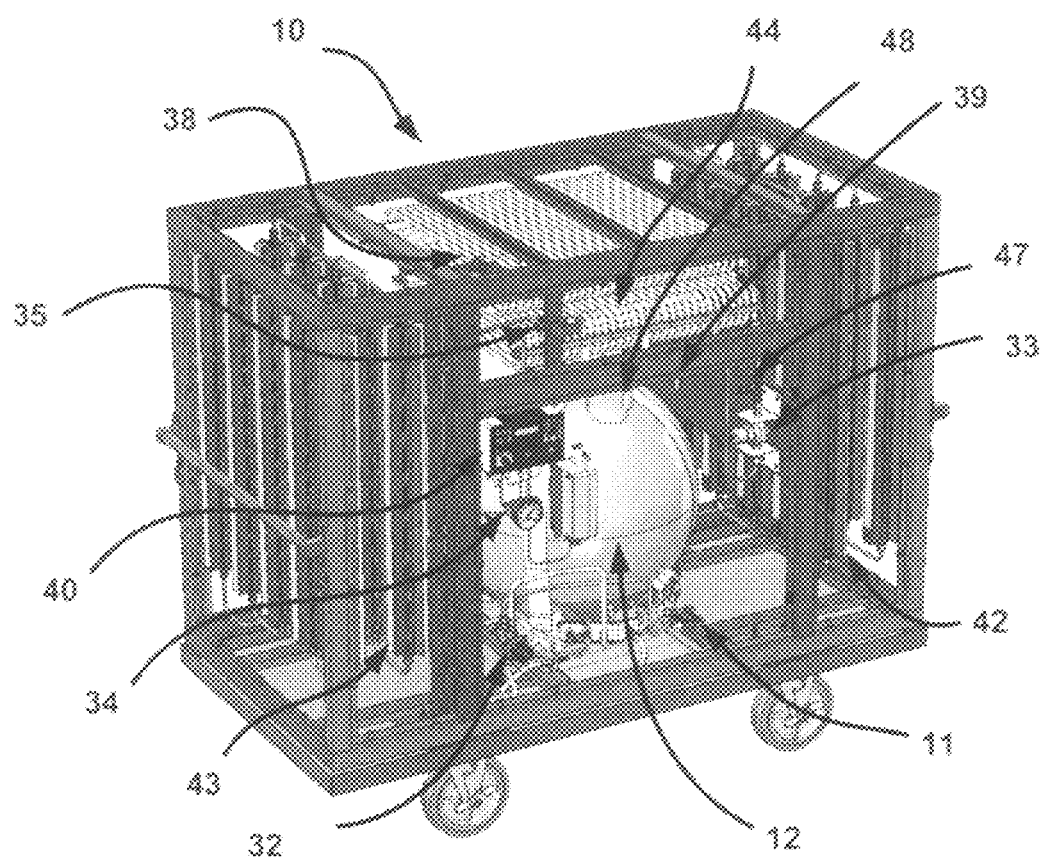
FIG. 3 is a front perspective view, of the mobile unit of the system with external panels removed.
Elements identified are:
10 (MODS 75 System)
11 (Burst Disc)
12 (Liquid Oxygen Converter)
32 (Filler Valve)
33 (Pressure Regulator)
34 (Outlet Pressure Gauge)
35 (Outlet Shut off & Vent Valve)
38 (Outlet Quick Disconnect Valve)
39 (Pressure Gauge Relief Valve)
40 (LOX Quantity Indicator and Alarm System)
42 (Vaporizer Bank 1)
43 (Vaporizer Bank 2)
44 (Dual Coil Heat Exchanger)
47 (Temperature Transducer)
48 (Pressure Transducer)
Figure 4:
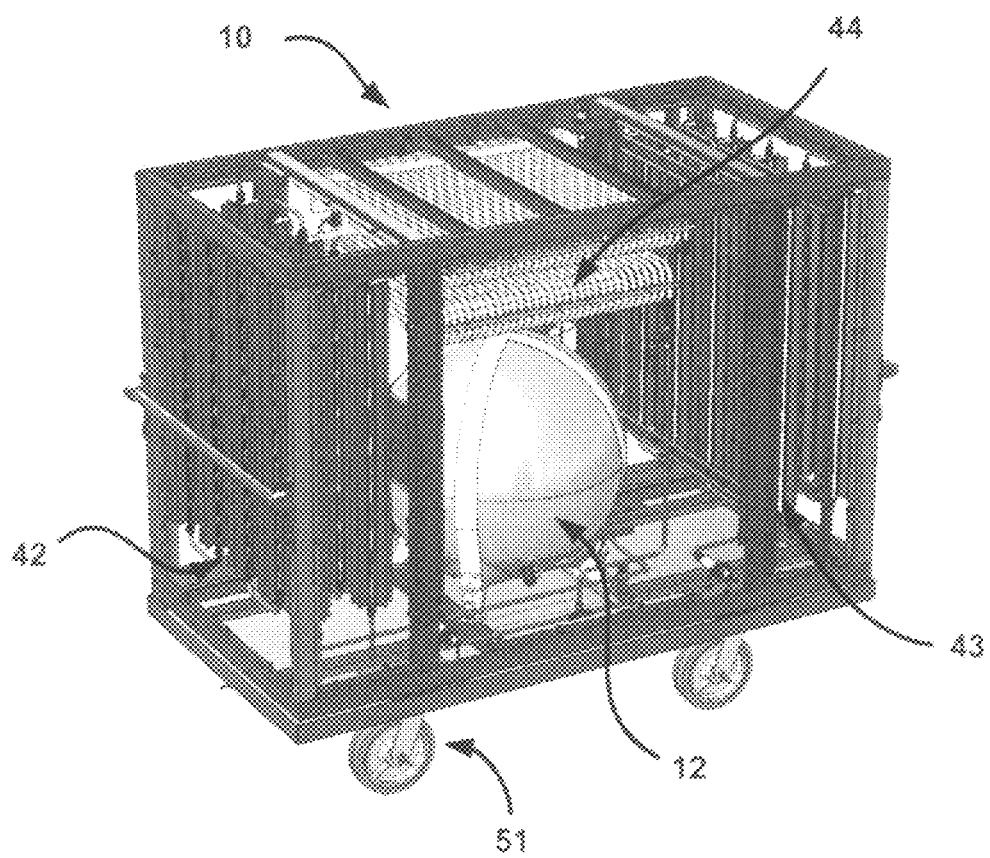
FIG. 4 is a back perspective view, of the mobile unit of the system with the panels removed.
Elements identified are:
10 (MODS 75 System Mobile Unit)
12 (Liquid Oxygen Converter)
28 (Check Valve VGL Port 1)
29 (Check Valve VGL Port 2)
31 (Safety Relief Valve)
36 (External VGL Port 1)
37 (External VGL Port 2)
38 (Outlet Quick Disconnect Valve)
42 (Vaporizer Bank 1)
43 (Vaporizer Bank 2)
44 (Dual Coil Heat Exchanger)

FIGS. 3 and 4 illustrate the arrangement of elements of the LOX converter (oxygen container) 12 within frame housing 55. Internal element of the system are illustrated and labeled in their proper orientation to each other, schematically, in FIG. 5. Individual system elements including valves, gauges and transducers, and fluid lines and connections, can be selected from available configurations or types, as specified according to the desired performance and rates which should be achieved, as herein described. The LOX quantity indicator and alarm system must be carefully designed for the present purposes. The specific arrangement of system 10 elements, as shown and described herein, is believed unique and heretofore entirely unknown.

The shutoff/vent feature 35, as an example of advantageous features, allow the outlet port to be shut off and, at the same time, vents all hoses and accessories and so provides a safety and convenience feature for disassembly of the system when it is to be shut down and taken out of use.

Referring to FIG. 5, and to FIG. 5A, which aids in the understanding, and now especially referring to FIG. 6, the oxygen converter 12 includes fluid lines and valve components connected within the converter 12 to fill the LOX container (FIG. 6) and to provide oxygen to other components in system unit 10. Components within the oxygen converter, including the LOX container 1, are shown schematically in FIG. 6. These internal elements are preferably assembled into a liquid oxygen converter for installation and service advantages, as the oxygen converter 12 can be removed as a unit, if desired, for service or replacement. Thus, internal components in addition to liquid oxygen container 1 are a supply line check valve 2, a pressure buildup coil 3, a primary relief valve 4, a secondary relief valve 5, and a pressure closing valve 8. If preferred, these internal elements could be incorporated directly into the LOX mobile system unit 10. The filler valve 32 (FIG. 5) is used to fill and buildup the pressure in the oxygen container 1. The specific arrangement of the fill valve 32, as shown in FIG. 1 and FIG. 3, is desirable for its ready access and convenient layout. However, other arrangements of this valve and mounting of such in a different location on system 10 may suffice. The filler valve 32 selected is designed to perform a combination function, which can be done with separate fill, buildup and vent valves. A burst disc 11 is connected to the LOX container 1 as a redundant safety device in the event of an excessive overpressure, and will not burst until a preselected high pressure would be reached, and which is not encountered in normal operation.

Referring now to FIG. 7 there is provided a schematic diagram of the liquid oxygen (LOX) quantity indicator and alarm system 40 with the various elements thereof shown and labeled, including LOX converter 12, LOX quantity indicator and alarm system 40. Temperature of oxygen leaving the dual heat exchanger is monitored by temperature transducer 41, while pressure in the oxygen supply is monitored by a pressure transducer 48. An AC adapter port 41 is also shown, and it permits AC line voltage to be connected to system unit 10 for operation under conditions in which the line voltage is available and where the system user (operator) prefers not to operate on the battery power internally provided. Safe operation is equally provided on battery pack power through the alarm system in which battery-driven microprocessor alarms provide pressure and temperature alarming with outlet pressure signaling to alert to need for VGL/source change-over.

With reference now to FIG. 8, there is provided a perspective view of internal components of the MODS liquid oxygen storage and delivery system mobile unit, with its external housing and various control and alarm components not shown. They are not shown so as to permit viewing of other components of the system.

FIG. 9 is a an overall system block diagram showing various interconnected components of the MODS liquid oxygen storage and delivery system including the mobile unit 10. Various components are connected for mass distribution of patient breathing oxygen. The HA and HRA components can be used as needed. Thus, shown connected to mobile system unit 10 is an interconnect hose by which oxygen under pressure is provided to a distributor block, so marked. The distributor block (DB) permits a multiple connection of other interconnect hoses, but only one hose is shown extending farther beyond, and leads to a 10-patient distribution unit. Such a unit is not further described as being beyond the need for present description of the use of system unit 10, but it is sufficient to note that up to ten patients may have breathing masks or inhalation units connected for receiving oxygen. Another hose extends beyond said 10-patient distribution unit, leading to yet another 10-patient distribution unit, and on to yet another such 10-patient distribution unit, so as to illustrate the sequential use of such units, each of which may have up to ten patients connected for receiving oxygen.

The MODS mobile unit has a fill valve 32, as shown in FIG. 1 and FIG. 3, to which an oxygen fill line of known type may be connected for filling or refilling or supplanting the mobile unit oxygen supply. This arrangement allows mobile unit vessel to be filled/refilled by large LOX storage/filling systems of the type that are commercially available, as by using a correct fill harness from a truck or trailer-mounted system, as by a known type of 50-gallon nurse trailer system. The fill valve in communication with the vessel thus allows oxygen to be provided from a main source thereof to the mobile unit when required, so as to fill, refill, or to supplement LOX in the vessel or to supplement distribution of breathing oxygen from the mobile unit.

When vessel 1 is filled with LOX, the MODS mobile unit can alone provide an uninterrupted supply of oxygen for distributed delivery to patients at a maximum flow rate of 450 liters per minute (LPM) maintaining a nominal operating pressure of 200 psig, to be further reduced at the point of delivery or by local regulator to suitable patient pressure and flow rate.

As is understood from the above description, the MODS mobile unit is also capable of operating by LOX supplied from external LOX sources such as independent variable gas/liquid (VGL) cylinders, and then distributing oxygen from the external LOX or VGL source. When using such external LOX cylinders, the MODS mobile unit will run indefinitely under normal operating conditions (indoors at room temperature) under conditions where the external LOX cylinders are rotated between each of multiple external-hookup ports of the MODS mobile unit. The system thereby provides long-term use without interrupting flow of oxygen to patients.

Accordingly, the system block diagram of FIG. 10 shows typical interconnected components of the MODS liquid oxygen storage and delivery system including the mobile unit, and where the mobile unit is shown being supplied with VGL oxygen sources respectively connected to one of the pair of oxygen inputs of the mobile MODS unit, as for replenishment or continued long-term operation by switching between VGL oxygen sources. The VGL sources may be, for example, 180 Liter oxygen tanks.

System Operational Features

The MODS mobile unit has two principal modes of operations. In a first independent mode, it is capable of supplying oxygen from it internal (on board) LOX tank, which is a dewar, a spherical high-pressure vacuum flask containing oxygen in liquid form. This LOX becomes gaseous at a temperature well below ambient temperature. The MODS mobile unit allows controlled heat to reach the cold interior of the LOX vessel so as to result in slow "boiling-off" of the LOX, while the main body of LOX under pressure remains liquid for a long duration.

In a second dependent mode, the MODS mobile unit allows connection to external liquid oxygen tanks for even more extended usage and patient distribution.

Extended Use Mode

The MODS system presently described has a unique system architecture that allows it to control and deliver 450 LPM flow of oxygen for long periods of time, while bring about desirable warming of the cold, gaseous oxygen exiting from the pressure vessel, so as to reach a desirable gas temperature for safe distribution to patients connected to the MODS system. The extended operating capability in the compact, mobile MODS mobile unit includes a complexed alternating multiple heat exchanger design with dual sets of vaporizers that allows a user, that is, the operator of the system, to connect commercial LOX storage tanks to the MODS mobile unit. While a first set of vaporizers is being used, it grows colder in use; and as is does so, a second set of vaporizers is warming up and becoming ready to be used again for warming cold, gaseous oxygen for patient use. Frost build-up on set of vaporizers does not interrupt operation as the other set of vaporizers achieves continuous operation and safe redundancy. By operator alternating of external LOX sources switching from one to another over periods of time, the system can run at high flow rates for an indefinite period, such as over a span of days. Switch-over by the operator can be conveniently accomplished by the user. For extended use the MODS can, as described above, be provided, for example, with source oxygen from a commercial LOX storage tank (having a pressure of 200 psig or more) connected to an external VGL port of the MODS mobile unit. Thus, a user who operates the system will for this purpose will take these steps:

1) Attach the end of the VGL harness assembly that contains the manifold assembly to the liquid outlet port on the LOX cylinder.
2) Attach the other end of the VGL harness assembly to the external LOX port on the back of the MODS.
3) By connecting the MODS the liquid line of the VGL, the user makes the system operational. Depending on the size of the VGL and the delivery rate, the MODS will supply oxygen flow for hours.
4) By connecting another VGL to the other external LOX port, the user enables extended operation from successive VGLs. When the first VGL is empty the user can open the second VGL whereby the MODS will use this tank as the fresh LOX source.

Pneumatic Description

Features of MODS operation, as involving extended operation from a typical external source (VGL), include:

1) LOX from the VGL enters MODS (VGL port 1) and immediately passes through a check valve shown. This check valve allows flow only from the VGL to MODS. Also the check valve allows the user to safely disconnect an empty VGL.
2) LOX that enters the MODS passes though a series, that is, a set or array of vaporizers dedicated to the VGL port 1 and the internal LOX container. The vaporizer array heats the LOX and so converts the LOX to a cold gas. As will be seen from FIG. 5, there are dual sets of vaporizer arrays, so that again, duality allows sequential supply to take place as one array experiences temperature changes of operation, and the other array normalizes to equilibrium temperature in readiness to handle flow when sources are switched. Frost build-up on one set, or array, of vaporizers heat exchanger does not interrupt operation and achieves safe redundancy.
3) The cold gas is feed into a dual coil heat exchanger to be warmed to a distribution temperature close to room temperature. The dual coil is highly efficient in warming the cold gas and is more efficient than a single coil heat exchanger such as heretofore known for warming cold breathing oxygen. The dual coil heat exchanger is not only markedly more efficient in warming the cold gas but has a lower pressure drop than would be the case if only a single coil heat exchanger were employed. The dual coil heat exchanger is found to be a significant improvement over a single coil heat exchanger and is highly important to the design of the new system.

After oxygen passes the heat exchanger its temperature is monitored by a transducer. The alarm system of the MODS is operatively responsive to the transducer. The alarm system triggers a visual caution alarm light if the outlet gas temperature reaches a first preselected caution threshold value, preferably approximately 0° F. The visual caution indicator is preferably a blinking yellow preliminary alert light. If the gas temperature should fall to a second preselected threshold value, preferably approximately −20° F., the alarm system triggers both an audible and visual warning alarm. The visual indicator energized is preferably a blinking red LED light. The user is then warned to reduce flow from the system to allow the outlet temperature to rise. The system will turn the respective alarms off when the outlet gas temperature rises to −5° F. or greater. The audible alarm for low temperature warning silences after the alarm mute switch is pressed. The audible alarm reactivates after a period of two minutes until the outlet gas temperature is above −5° F. In this way, there is provided outlet gas low temperature caution and warning safety alarms so that the system provides protection to patient from cold gas. The temperature alarm has a mute feature, by which the authorized operator may silence the alarms after having been warned.

4) Has a LOX quantity indicator for the internal LOX tank. Quantity indicator has a low liquid level alarm for the operator.
5) The MODS oxygen pressure is regulated to an outlet pressure of preferably approximately 200 psig. The MODS system mobile unit has a pressure gauge. A pressure transducer monitors the outlet pressure. The pressure transducer is connected to the alarm system that triggers an audible and visual outlet gas pressure alarm if the outlet gas pressure falls to approximately 100 psig. The visual indicator is a blinking red LED light. The outlet gas pressure alarm allows a user to determine when to switch the external tanks. The gas pressure alarms has also the mute feature so that the operator may silence this or other alarms after having been warned.

6) Before reaching the outlet disconnect, the regulated oxygen is directed to a shutoff/vent valve. It valve allows for oxygen flow from the MODS to be turned off and it also safely vents the hoses and accessories. After the hoses and accessories are vented to atmosphere, the user can safely disconnect the hoses and accessories.

Operation of the MODS mobile unit using its internal storage involves these features:

1) The MODS 75 has a 75 Liter internal LOX storage container 1. This container can be filled with or without external tanks connected. As the on board LOX in is distributed by the mobile unit, many hours of breathing oxygen are provided.
2) When the internal tank is filled the tank will build up pressure. The MODS mobile unit will first use the LOX storage container with the highest pressure.
3) The internal tank is connected to the same vaporizers used for the VGL 1 port.
4) The MODS when using the internal tank operates with the same pressure and warning system functioning as when the MODS is supplied by an external tank.
5) Just before the outlet disconnect the gas in the system is directed by a shutoff/vent valve. This valve allows for the flow from the MODS mobile unit to be turned off and vents the hoses and accessories. After the hoses and accessories are vented to atmosphere, the user can safely disconnect them.
6) The MODS mobile unit delivers oxygen indefinitely by alternating the oxygen from one VGL connection to the other VGL connection. It provides an ability to fill on board LOX while simultaneously delivering oxygen to patients.

These and others of the advantages of the new MODS LOX system are especially noteworthy but one can very much appreciate especially that the new mobile unit delivers oxygen indefinitely by alternating the oxygen from one VGL connection to the other VGL connection. Dual vaporizers allow switching immediately from one external source to another. Thus, breathing oxygen is seamlessly and continuously provided without interruption even after the relatively immense on board LOX is used. Moreover, the system provides an ability to fill/refill on board LOX while simultaneously delivering oxygen to patients, again without interruption. The use of a dual coil heat exchanger means that frost build-up on the heat exchanger does not interrupt operation. The battery-driven microprocessor alarms with pressure and temperature alarming with outlet pressure signaling alert to the need for VGL/source change-over. The low temperature caution alarm and outlet gas pressure warning alarm provide protection to patient from cold oxygen and from loss of pressure no matter whether few or many patients are using the system. The large 75-liter on board LOX storage provides a hospital-type flow of many hours before supplementing, as by VGL resupply, will be needed. Safe and effective mass distribution of breathing oxygen is thus assured in a situation such as a mass casualty incident where many patients need emergency oxygen in a location where, for example, patients, even if widely located about the location, will be given medical attention for an indefinite period whether of a few hours or many hours. A great need is thereby fulfilled. After use, the shutoff/vent feature allow the outlet to be shut off and vent all hoses and accessories at the same time, so safely allowing system disassembly.

As various modifications could be made in the constructions and methods herein described and illustrated without departing from the scope of the invention, it is intended that all matter contained in the foregoing description or shown in the accompanying drawings shall be interpreted as illustrative rather than limiting.

What is claimed is:

1. A mass oxygen distribution system (MODS) for mass delivery and distribution for of breathing oxygen, the system comprising:

a MODS mobile unit for storing a large amount of liquid breathing oxygen (LOX), meaning about at least 75 L of LOX, within an enclosure of the MODS mobile unit for controlling the distribution of oxygen from said enclosure at safe pressure for being mass-distributed to one or more end users;

A LOX on board oxygen source within said enclosure having at least one pressurized vessel in which a relatively large amount of oxygen, meaning about at least 75 L of LOX, is maintained in a liquid state (LOX) in readiness for being volatilized to provide oxygen in vapor form for many hours of said distribution;

the enclosure being supported by wheeled support members for allowing the enclosure to be moved to and through premises where mass distribution to said one or more end users is required;

the enclosure being substantial in size but precisely dimensioned for being capable of fitting easily though passageways and doorways of a wide range of premises where mass distribution could be required;

a fill port of the enclosure for filling of the LOX converter;

a fill valve communicating with the fill port and in communication with the oxygen converter for providing oxygen from a main source thereof to the oxygen converter to provide LOX to the pressurized vessel for distribution by the mobile unit, a fluid line providing liquid oxygen from the pressurized vessel to be changed to vapor form;

vaporizer array provision within the enclosure for converting the liquid oxygen to cold gaseous breathing oxygen;

heat exchanger provision within the enclosure for warming the cold gaseous breathing oxygen to safe breathing temperature;

dual input ports of said enclosure adapted for receiving oxygen alternately from external auxiliary oxygen sources such as VGL (variable gas/liquid) storage, whereby said system is capable of supplying breathing oxygen at controlled high flow rates and at controlled temperature and pressure for an extended period of time by use of either on board oxygen storage or external oxygen sources;

the vaporizer provision comprising dual independent sets of vaporizers that allows an operator of the system to switch between said external auxiliary oxygen sources, with use of one of the sets of vaporizers for each auxiliary oxygen source;

said system permitting filling/refilling of the on board LOX source when receiving oxygen from external auxiliary oxygen source such as VGL source, while at the same time supplying continuous breathing oxygen output to patients.

2. A mass oxygen distribution system as set forth in claim 1, the heat exchanger provision comprising a dual coil heat exchanger such that heat exchanger frost build-up does not interrupt supply of oxygen.

3. A mass oxygen distribution system as set forth in claim 1 wherein while a first set of the vaporizers is being used, it grows colder in use; and as is does so, the second set of the vaporizers is warming up and becoming ready to be used again for warming cold, gaseous oxygen for patient use, and wherein frost build-up on one set of vaporizers does not interrupt operation as the other set of vaporizers thereby to achieve continuous operation and safe redundancy.

4. A mass oxygen distribution system as set forth in claim 3 wherein at least one of the sets of vaporizers is used for vaporizing liquid oxygen from the on board LOX source when the mobile unit is operated to provide oxygen from the pressurized vessel instead of the auxiliary sources.

5. A mass oxygen distribution system as set forth in claim 1 wherein said mobile unit includes audible and visual warning alarm system within the enclosure for alerting an operator user of a possibility of an undesirable condition of oxygen flow to patients.

6. A mass oxygen distribution system as set forth in claim 5 wherein said warning alarm system is a battery-operated microprocessor alarm system responsive to undesirable change in pressure or temperature of oxygen flow to patients.

7. A mass oxygen distribution system as set forth in claim 5 wherein said warning alarm system is operative to warn the operator to reduce oxygen flow from the system if gas temperature drops below a predetermined value, so as to allow the operator to cause the outlet temperature to rise, whereby to protect patients from oxygen that is too cold.

8. A mass oxygen distribution system as set forth in claim 5 wherein said warning alarm system is operative to warn the operator in the event of reducing oxygen delivery pressure, so as to alert the operator to need for changing to an auxiliary oxygen source, or to switch between different auxiliary oxygen sources.

\* \* \* \* \*